United States Patent [19]

Reich

[11] Patent Number: 4,790,042

[45] Date of Patent: Dec. 13, 1988

[54] BABY COMFORTER

[76] Inventor: Beth A. Reich, 620 Horton St., Greenwood, Ind. 46142

[21] Appl. No.: 104,221

[22] Filed: Oct. 5, 1987

[51] Int. Cl.[4] .......................................... A47C 20/02
[52] U.S. Cl. .......................................... 5/437; 5/442
[58] Field of Search ................... 5/417, 420, 436, 437, 5/441, 442, 485, 490, 431, 82 R; 128/134

[56] References Cited

U.S. PATENT DOCUMENTS

| | | |
|---|---|---|
| 1,558,278 | 10/1925 | Phillips . |
| 1,651,561 | 12/1927 | Storey . |
| 2,289,726 | 7/1942 | Prespare . |
| 2,449,741 | 9/1948 | Fitzpatrick . |
| 2,497,443 | 2/1950 | Eatman . |
| 2,675,557 | 4/1954 | Kempner, Jr. . |
| 2,961,668 | 11/1960 | Hayes ................................ 5/434 |
| 3,467,085 | 9/1969 | Cornier ......................... 128/134 X |
| 3,566,864 | 3/1971 | Garrow . |
| 3,623,485 | 11/1971 | Price . |
| 3,741,207 | 6/1973 | Fuson . |
| 3,815,610 | 6/1974 | Winther . |
| 3,882,873 | 5/1975 | Arango . |
| 3,889,684 | 6/1975 | Lebold . |
| 3,950,789 | 4/1976 | Konz et al. . |
| 4,033,354 | 7/1977 | DeRosa . |
| 4,034,748 | 7/1977 | Winner ........................... 5/82 R X |
| 4,204,543 | 5/1980 | Henderson . |
| 4,382,446 | 5/1983 | Truelock et al. . |
| 4,568,298 | 2/1986 | Acree . |
| 4,604,987 | 8/1986 | Keltner ............................. 5/421 X |
| 4,606,087 | 8/1986 | Alivizatos ........................ 5/420 X |

FOREIGN PATENT DOCUMENTS 931649  7/1963  United Kingdom ................... 5/421

Primary Examiner—Gary L. Smith
Assistant Examiner—Trettel Michael F.
Attorney, Agent, or Firm—Barnes & Thornburg

[57] ABSTRACT

A baby comforter constructed of textile material and which includes a body portion with a pocket. Two arms and a crotch strap are attached at one end to the body portion, the free ends of the arms and straps can be joined together over the body portion to form a restraint harness for an infant. The arms are formed from hollow textile covers that enclose deformable rods such that the arms can be selectively bent and formed to accommodate babies of differing sizes.

2 Claims, 1 Drawing Sheet

BABY COMFORTER

BACKGROUND AND SUMMARY OF THE INVENTION

This invention relates to baby comforters. Various types of comforters are known. There are, for example, the comforters of U.S. Pat. Nos. 1,558,278 and 4,568,298. There are also various types of attachment and restraint mechanisms, many directed specifically toward children. Examples of such mechanisms are those described in U.S. Pat. Nos. 1,651 561; 2,289,726; 2,449,741; 2,675,557; and 3,566,864. There are also various forms of hot- and cold-pack attachment mechanisms for attaching heat sources and heat sinks to the body which are directed primarily toward adults. Examples of such mechanisms are those described in U.S. Pat. Nos. 2,497,443; 3,623,485; 3.815,610; 3,882,873; 3,889,684; 3,950,789; 4,033,354; 4,204,543; and, 4,382,446. Further, there are mechanisms for restraining body parts in particular orientations for therapeutic purposes. Examples of such devices are the ones illustrated in U.S. Pat. No. 3,741,207.

It is well established that babies enjoy being held and generally do not like to be left alone. They seem to miss the warmth of another person holding them, even when they are about to fall asleep. Additionally, sometimes a baby's stomach is upset. Occasionally, the application of warmth seems to relieve a baby's upset stomach. A hot water bottle can be used to apply warmth, but a mechanism is needed to attach the hot water bottle to the baby, who may change positions frequently during a nap or through the night.

The present invention is intended to meet these objectives. It is intended to give the baby a sense of being held by another person. This is achieved through the mechanism by which the apparatus of the invention is secured to the baby and by the ability of the apparatus to accommodate, and gently apply warmth to the baby from, a hot water bottle.

According to the invention, a baby comforter comprises a body portion, a crotch strap and two arms. Each of the crotch strap and two arms includes a proximal end and a distal end. The proximal ends of the arms are attached to the body portion in generally opposed orientation. The proximal end of the crotch strap is attached to the body portion at a point generally equidistant from the proximal ends of the two arms. The distal ends of the crotch strap and two arms are provided with means for selectively attaching the distal ends of the crotch strap and two arms to each other to encompass the baby and give it the feeling of being held.

Illustratively, the body portion includes means defining a pocket which can accommodate a hot water bottle or the like.

Additionally, according to the invention, the arms include somewhat tube-shaped covers and selectively formable cores within the covers. The cores are formable to fit snugly around babies of different sizes.

Further, illustratively, the means for selectively joining the distal ends of the two arms and the distal end of the crotch strap comprises hook-and-eyelet type material, such as VELCRO-type material.

In the illustrated embodiment, the body portion, arm covers and crotch strap are all made from textiles.

The invention may best be understood by referring to the following description and accompanying drawings which illustrate the invention. In the drawings.

Figure 1:
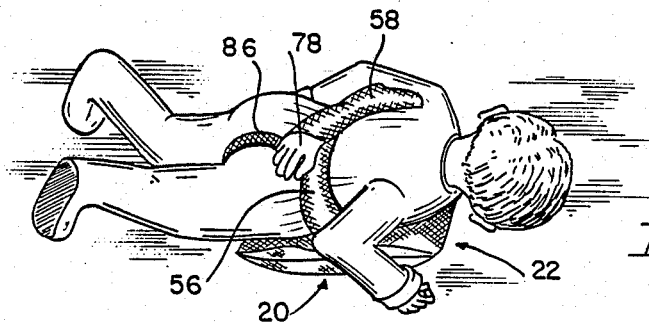
FIG. 1 illustrates a perspective view of an apparatus according to the invention fastened about a baby.
Figure 2:
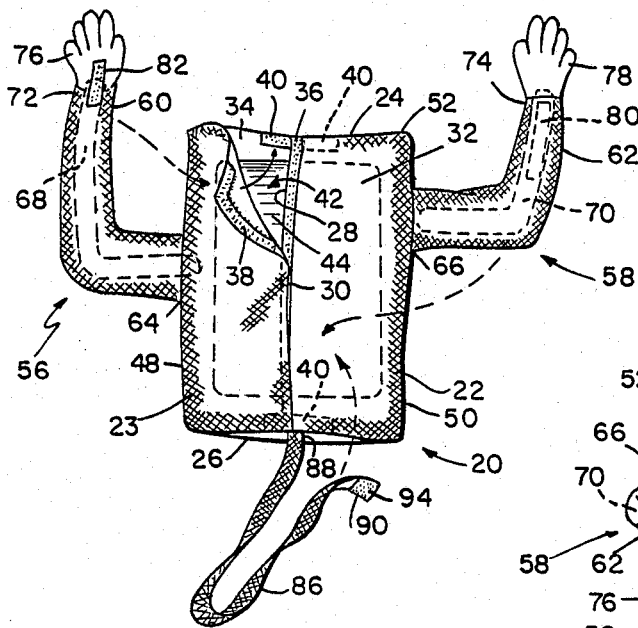
FIG. 2 illustrates a plan view of one side of the apparatus of FIG. 1 with the arms and crotch strap open to receive a baby.
Figure 3:
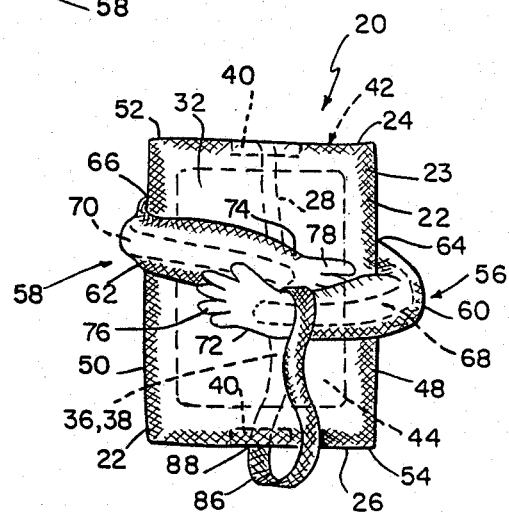
FIG. 3 illustrates a plan view of the opposite side of the apparatus from that illustrated in FIG. 2 with the arms and crotch strap in the orientation illustrated in FIG. 1.

The apparatus 20 of FIGS. 1–3 includes a body portion 22 which is constructed from a generally rectangular piece of soft, washable, durable cloth 23 having longer side edges 24, 26, shorter end edges 28, 30, and opposite faces 32, 34. A length 36 of one of the complementary forms of VELCRO-type hook-and-eyelet material, for example, hooks, is attached adjacent end edge 28 on face 32. A length 38 of the complementary form of hook-and-eyelet material, for example, eyes, is attached adjacent end edge 30 on face 34. A small length 40 of the complementary form of hook-and-eyelet material is also attached to each of side edges 24, 26 on face 32 at about the mid-point of the respective side edge 24, 26. The cloth 23 can this be folded in the manner of a portfolio to form a pocket 42 for receiving a hot water bottle 44 or the like. The hot water bottle 44 is kept from sliding out of the pocket 42 by the engagement of strips 36, 38 and also by the engagement of strips 36, 40, 40.

When the cloth 23 is folded as described above, opposed side edges 48, 50 and opposed end edges 52, 54 of body portion 22 are formed. A respective arm 56, 58 is attached to each of opposed side edges 48, 50 in generally opposed orientation. The illustrated arms 56, 58 are slightly offset from each other along their respective side edges 48, 50. Each arm 48, 50 is provided by a cloth tube 60, 62 having a proximal end 64, 66, respectively, by which it is sewn to a respective side edge 48, 50. A selectively deformable rod 68, 70, respectively, is inserted into a respective cloth tube 60, 62 and the distal ends 72, 74, respectively, of tubes 60, 62 are closed by sewing hand-shaped pieces of cloth 76, 78 respectively, to them. The rods 68, 70 illustratively are STYLING STIX TM devices available from Mercury Foam Corp., Consumer Products Division, Hackensack, N.J. 07601.

A strip 80 of hook-and-eyelet material, for example, hooks, is attached to the outside (side away from baby when the arms 48, 50 encircle the baby) of arm 58. A small patch 82 of complementary hook-and-eyelet material, for example, eyelets, is attached to the inside of hand-shaped piece of cloth 76. Additionally, a length 86 of cloth webbing material has its proximal end 88 attached to end edge 54 of body portion 22. A small patch 90 of hook-and-eyelet material which will interconnect with strip 80 is attached to the distal end 94 of webbing material 86.

In use, cloth 23 is first spread open and hot water bottle 44 is placed on it. Cloth 23 is then folded about hot water bottle 44 as described above and the hook-and-eyelet strips 36, 38, 40, 40 are engaged, capturing the hot water bottle 44 in the pocket 42. The comforter 20 is then turned over and the baby is laid, stomach down, on it. The arms 48, 50 are bent into a suitable curvature to encircle the baby. The crotch strap 86 is then brought up between the baby's legs and the hookand-eyelet strip 80 and patches 82, 90 are engaged, fastening the comforter about the baby.

What is claimed is:

1. A baby comforter comprising a body portion including means defining a pocket, the body being constructed at least in part from a textile or textile-like material, a crotch strap, and two arms, each of the crotch strap and arms having a proximal end and a distal end, means for attaching the proximal ends of the arms in opposed orientation on the body, means for attaching the proximal end of the crotch strap to the body at a point generally equidistant from the locations at which the proximal ends of the two arms are attached to the body, and means for selectively joining the distal ends of the two arms and the distal end of the crotch strap, the joining means provided adjacent the remote ends of the arms and crotch strap, the arms comprising textile or textile-like material covers and selectively formable cores formed by deformable rods within the covers, the cores being formable to accommodate babies of different sizes.

2. The apparatus of claim 1 wherein the means for selectively joining the distal ends of the two arms and the distal end of the crotch strap comprises hook-and-eyelet type material.

* * * * *